(12) United States Patent
Carr

(10) Patent No.: US 7,943,724 B2
(45) Date of Patent: May 17, 2011

(54) PROCESS FOR PREPARING DIAMINODIPHENYLMETHANES

(75) Inventor: Robert Henry Carr, Bertem (BE)

(73) Assignee: Huntsman International LLC, The Woodlands, TX (US)

( * ) Notice: Subject to any disclaimer, the term of this patent is extended or adjusted under 35 U.S.C. 154(b) by 412 days.

(21) Appl. No.: 12/095,967

(22) PCT Filed: Nov. 7, 2006

(86) PCT No.: PCT/EP2006/068171
§ 371 (c)(1),
(2), (4) Date: Jun. 3, 2008

(87) PCT Pub. No.: WO2007/065767
PCT Pub. Date: Jun. 14, 2007

(65) Prior Publication Data
US 2008/0312405 A1    Dec. 18, 2008

(30) Foreign Application Priority Data

Dec. 8, 2005  (EP) .................................... 05111828

(51) Int. Cl.
*C08G 12/08* (2006.01)
*C08G 12/00* (2006.01)
*C07C 211/50* (2006.01)
*C07C 211/00* (2006.01)

(52) U.S. Cl. ........ 528/269; 528/482; 528/489; 528/499; 528/502 R; 528/503

(58) Field of Classification Search .................. 528/269, 528/482, 489, 499, 502 R, 503; 564/333
See application file for complete search history.

(56) References Cited

U.S. PATENT DOCUMENTS

| 3,277,173 A | 10/1966 | Powers et al. |
| 3,362,979 A | 1/1968 | Bentley |
| 3,676,497 A | 7/1972 | Recchia et al. |
| 3,804,849 A | 4/1974 | Griss et al. |
| 3,825,598 A | 7/1974 | Eifler et al. |
| 4,039,580 A | 8/1977 | Frulla et al. |
| 4,039,581 A | 8/1977 | Frulla et al. |
| 4,297,294 A | 10/1981 | Mango |
| 5,207,942 A | 5/1993 | Scherzer et al. |
| 6,010,612 A | 1/2000 | Freire et al. |
| 6,433,219 B1 | 8/2002 | Strofer et al. |
| 6,576,788 B1 | 6/2003 | Penzel et al. |
| 6,673,970 B1 | 1/2004 | Renbaum et al. |
| 6,916,953 B2 | 7/2005 | Walsdorff et al. |
| 7,041,776 B2 | 5/2006 | Koch et al. |
| 2003/0045745 A1 | 3/2003 | Hagen et al. |
| 2004/0171869 A1 | 9/2004 | Reif et al. |
| 2005/0222291 A1 | 10/2005 | Pirkl et al. |

FOREIGN PATENT DOCUMENTS

| DE | 295628 | 7/1991 |
| EP | 003303 | 8/1979 |
| EP | 031423 | 7/1981 |
| EP | 876335 | 11/1998 |
| EP | 1403242 | 3/2004 |
| EP | 1561746 | 8/2005 |
| GB | 1167950 | 10/1969 |
| GB | 1365454 | 9/1974 |
| GB | 1378423 | 12/1974 |

OTHER PUBLICATIONS

Lowenkron, Steven, "Amines, aromatic, methylenediamine", Kirk-Othmer Encyclopedia of Chemical Technology, 1992, pp. 1-11.

*Primary Examiner* — Duc Truong
(74) *Attorney, Agent, or Firm* — Robert A. Diaz

(57) ABSTRACT

Process for preparing diamino diphenyl methane and poly-(diamino diphenyl methane) comprising reacting aniline with formaldehyde in the presence of hydrogen chloride added in the gaseous form wherein the aniline contains 0.1 to 7 wt %, preferably 2 to 5 wt % of a protic chemical, preferably water.

3 Claims, No Drawings

PROCESS FOR PREPARING DIAMINODIPHENYLMETHANES

CROSS REFERENCE TO RELATED APPLICATIONS

This application is the National Phase of International Application PCT/EP2006/068171 filed Nov. 7, 2006 which designated the U.S. and which claims priority to European (EP) Pat. App. No. 05111828.9 filed Dec. 8, 2005. The noted applications are incorporated herein by reference.

Methylene diphenylene diisocyanate isomers (MDI) and the mixtures of the diisocyanates with higher molecular weight homologues known as poly-(methylene diphenylene di-isocyanate) (hereinafter PMDI) are widely used as speciality binders for various composite materials, with polyamines for polyureas and, together with polyether and polyester polyols, to form the diverse range of polyurethane materials including cross-linked rigid foams for insulation, flexible foams for automotive seating and furniture and as elastomers & coatings. PMDI is conventionally produced by phosgenation of the corresponding mixture of polyamines known as poly-(diamino diphenyl methane) (hereinafter DADPM) formed from condensation of aniline and formaldehyde.

Methods for the production of DADPM are numerous and varied. Condensation of aniline and formaldehyde (as the aqueous solution called formalin, as gaseous formaldehyde or as the solid paraformaldehyde) can take place in neutral, basic or acidic conditions, though conversion through to the polymeric primary amine mixture invariably requires the use of acidic species.

Condensation of aniline with formaldehyde under neutral or basic conditions, with subsequent optional separation of water and, additionally, optional further drying of the condensate has been widely described. The so-called neutral condensate, containing N,N'-methylene di-aniline (aminal) and possibly other anilinoacetals is then subsequently converted to secondary amines and the final primary amine mixture by using acidic species. Heterogeneous solid acid catalysts have been described (e.g. in U.S. Pat. Nos. 3,362,979; 4,039,580 and 4,039,581), as have a range of homogeneous acids and, predominantly, aqueous mineral acids especially aqueous hydrochloric acid. Aniline hydrochloride solid (see, e.g., U.S. Pat. No. 4,297,294 and EP 0003303) and gaseous hydrogen chloride (U.S. Pat. No. 3,676,497) have also been described. Difficulties with such processes include the additional production stages, leading to greater process complexity and, in the case of heterogeneous catalysts, regeneration or disposal of the contaminated solids. Condensation of aniline and formaldehyde under acidic conditions produces directly the secondary amines which are subsequently converted to the desired primary amines by the already-in-place catalyst. An anhydrous process has been described using aniline hydrochloride salt as the catalyst (see GB 1167950), but mobility problems with the resulting mixture required addition of further aniline, thereby precluding reaction at the desired aniline/formaldehyde ratio.

Problems with precipitating aniline salt were also found in an acidic aniline/formaldehyde condensation process (described in U.S. Pat. No. 3,825,598). Prior art described therein solved the problem by addition of extra water, thereby increasing effluent from the process. The disclosed invention solved the potential solids problem by separating the amine/catalyst mixture into two portions, adding the formaldehyde to a first portion and subsequently adding the second portion, thereby increasing the process complexity.

By far the most numerous in commercial use for DADPM production are methods using aqueous hydrochloric acid, predominantly because of its relatively low cost, widespread availability and ease of disposal of catalyst neutralised with sodium hydroxide to give aqueous solutions of sodium chloride (brine).

Variations on the DADPM production process using hydrochloric acid include variations of the proportions of reactants and catalyst, variations in the form of the reactants, variations of the order and method of mixing the components, variations in the temperatures and pressures in different parts of the process, variations in operation of the reaction sections of plant and variations in work-up of the product and effluent streams, variations of the process type (batch, continuous, semi-continuous), variations of the process equipment and variations in the combinations of those variations. This plethora of processes have all been employed to affect the relative amounts of the major components of the polymeric DADPM mixture, to affect the levels of various impurity species such as N-methylated groups, and to improve the economics of the process.

The chemical requirements of the hydrochloric acid catalysed production of DADPM are aniline, a methylene-group source (formaldehyde in some physical form) and hydrogen chloride. The other major component present is water.

The amount of water produced by the required condensation reaction is determined by the choice of stoichiometry of the reactants, but significant quantities of additional water are present from the normally used aqueous formalin and the aqueous hydrochloric acid. Significant economic benefits could result by reduction of the amounts of this extra water because of reduction of the total volume of reaction mixture and, hence, more efficient use of whatever process equipment is used. Also, less water results in a relatively higher catalyst concentration, thereby increasing reaction rates and improving throughput. In addition, reduction in the amount of the extra water minimises the size of all the various process equipment required to separate and work-up the waste water (brine) streams prior to disposal. The economic benefits arise from reduction in the amount of neutralising sodium hydroxide relative to the amount of DADPM produced, reduction in equipment size, reduction in number of plant items, avoidance of a brine concentration step for low acid recipes, simplicity and robustness of operation of the process.

The amount of extra water present can be reduced by changing the formaldehyde source or the hydrogen chloride source or both. Formaldehyde can be employed without water as either a gas or as solid paraformaldehyde. In the case of formalin, the amount of water can be reduced by increasing the solution strength. Aqueous hydrochloric acid is normally available commercially as the 30 to 33 weight percent (wt %) solution of HCl in water and production processes previously described frequently use such or similar concentrations.

The solubility of aniline hydrochloride in aniline is limited to levels below 5 wt % at temperatures typically used for the catalysed aniline/formaldehyde condensation stage in DADPM production (up to maximum of 75° C.). This means that if gaseous hydrogen chloride is reacted with aniline, solid aniline hydrochloride forms before the level of the catalytic species reaches the level typically required for economic operation of the DADPM process. Solid aniline hydrochloride would be deleterious for commercial scale process operation because of the potential for fouling and blocking process equipment and due to potential variations in catalyst levels through time due to variable deposition and subsequent break up of solid deposits. So, although the use of gaseous hydrogen chloride is an obvious alternative variation of DADPM production (see, e.g., US 2004/0171869, U.S. Pat. Nos. 6,576,788, 5,207,942, 3,804,849, GB 1365454 and EP 0031423), aqueous hydrochloric acid is invariably used. Thus, there still exists a need to use gaseous hydrogen chloride as the source of catalyst for production of DADPM in order to achieve the benefits from reducing the amount of water in the process but without encountering the problems of having insufficient catalyst present for commercial rates of operation or formation of deleterious solids.

It is therefore an object of the present invention to provide a new process for the use of gaseous hydrogen chloride as the source of acid catalyst for the acid catalysed condensation of aniline and formaldehyde, with subsequent conversion to the DADPM mixture of primary amines which ultimately becomes the commercially important PMDI by means of phosgenation.

It has now surprisingly been found that such as process can be operated by absorbing hydrogen chloride gas into aniline which contains a low, but significant quantity of protic chemical, preferably water. This amount of water is lower than would be present from creating the same aniline/HCl ratio using aniline and the most concentrated aqueous hydrochloric acid possible.

The process of the present invention has the further advantage that it can utilise the hydrogen chloride produced as the by-product of the conversion of DADPM to PMDI by phosgenation, in comparison to prior art where the HCl is used to produce chlorine via complex processes (as disclosed in EP 0876335 and U.S. Pat. No. 6,916,953, for example) or is simply absorbed into water to make aqueous hydrochloric acid. In addition, the equipment necessary to make use of gaseous HCl can be readily fitted to existing conventional commercial DADPM manufacturing units, thereby minimising equipment modification costs and obviating the need for totally different process designs & equipment. The process of the present invention also has a beneficial effect on the color of the MDI derived from the thus obtained DADPM.

Hence the present invention provides a process for preparing diamino diphenyl methane and poly-(diamino diphenyl methane) [DADPM] comprising reacting aniline containing catalyst with formaldehyde, where the source of the catalyst is gaseous hydrogen chloride which has been absorbed into aniline wherein the aniline contains 0.1 to 7 wt %, preferably 2 to 5 wt % of a protic chemical, preferably water.

Other suitable protic chemicals include, but are not limited to, aliphatic and aromatic alcohols such as methanol, ethanol, benzyl alcohol, cyclohexanol and phenol, other alcohols and other types of chemicals such as carboxylic acids, etc.

The exact quantity of water to be contained in the aniline depends on the desired aniline/formaldehyde/HCl recipe needed and the temperature at which the aniline/HCl/water mixture is to be reacted with the formaldehyde, this reaction temperature being chosen as part of the well established prior art for controlling the final DADPM product composition and levels of impurities containing N-methyl, formate and quinazoline functional groups (see, for example, "The Chemistry and Technology of Isocyanates", Henri Ulrich, John Wiley & Sons Ltd., 1996 ISBN 0-471-96371-2).

The exact upper limit of how much HCl can be dissolved in the aniline/water mixture depends also on the purity of the aniline. For example, the presence of minor amounts of aniline process impurities such as cyclohexanol can increase slightly the solubility limit for adding gaseous HCl before forming solids.

A wide range of aniline/formaldehyde/HCl recipes have been used to produce DADPM and there is extensive prior art documenting these.

Commonly used aniline:formaldehyde ratios are in the range 1.80:1.00 to 5.00:1.00, preferably 2.10:1.00 to 2.75:1.00 whilst formaldehyde: HCl ratios are typically 1.00:0.01 to 1.00:2.00, preferably 1:00:0.1 to 1.00:0.60.

The process is normally carried out by mixing the aniline and acid, frequently with cooling, followed by addition of the formaldehyde, optionally in stages. Many process variations are known: batch, continuous, semi-continuous.

Temperature control over the entire process is well known to impact the final composition of the DADPM mixture, especially in terms of isomer variations, such as the relative quantities of the 4,4'-, 2,4'- and 2,2'-diamine isomers as well as impacting the relative amounts of homologues, in addition to the overall aniline:formaldehyde ratio. Temperature ranges are generally from 50 to 150° C., preferably from 60 to 140° C. often with staged increments through the process such that conversion of intermediate secondary amine species is driven to low levels at the end of the process (typically less than 1 wt %, preferably less than 0.1 wt % defined in terms of relative amounts of total aliphatic functional groups as determined by 1H NMR spectroscopy of the deuterium oxide exchanged solution of the DADPM product in deuterated dichloromethane).

According to a particular embodiment the process of the present invention comprises the following steps:
(i) preparation of an aniline/water mixture with controlled water content typically 0.1 to 7 wt %, preferably 2 to 5 wt % of water;
(ii) absorption of hydrogen chloride gas, optionally from a phosgenation process, into the aniline/water mixture, optionally with cooling to a desired temperature;
(iii) addition, optionally with simultaneous mixing, of formaldehyde into the aniline/HCl/water mixture in one or more stages, optionally with cooling, to yield an intermediate mixture;
(iv) heating said intermediate to predetermined levels generally from 50 to 150° C., preferably from 60 to 140° C., optionally in staged increments through the process to produce the desired mixture of primary amine isomers and homologues known as DADPM;
(v) working up said mixture by neutralisation of the acid typically with sodium hydroxide solution, separation and washing of the organic and brine phases, followed by removal and recycling of excess unreacted aniline.

According to another embodiment of the present invention the above 5 steps are followed by the following steps in order to prepare PMDI:
(vi) dissolving the worked-up DADPM in solvent, typically chlorobenzene, with phosgene, also optionally in the presence of solvent, to produce PMDI;
(vii) working up and separating by known methods the PMDI product into the range of di-isocyanate isomers and PMDI mixtures.

The phosgenation reaction can be carried out by any of the many and well known variations described in the prior art.

For example, the DADPM can be dissolved in chlorobenzene to a level of typically 10 to 40 wt %, preferably 20 to 30 wt %, the resulting solution then being introduced into reaction vessels typically by means of special mixing devices by means of which the amine blend is thoroughly and intimately mixed with phosgene, also optionally in solution, preferably in the same solvent as the DADPM.

Reaction temperature at this stage is typically in the range 50 to 150° C., preferably 75 to 95° C. The product of this initial reaction stage may be worked up immediately or there may be additional reaction, optionally in additional reaction vessels, optionally including addition of phosgene, for further digestion of reaction intermediates and/or by-products. Many pressure and temperature regime variations are known from the prior art and many variations in process equipment can be employed.

On completion of the phosgenation reaction, the crude MDI product can be separated from excess phosgene, product HCl, and reaction solvent by any means known to those skilled in the art, typically by distillation, and subjected to further work up such as the well established thermal cracking of impurity compounds known as "dechlorination". The mixture of di-isocyanate isomers and PMDI homologues can be used as such or further refined to give various di-isocyanate or polymeric MDI products, typically by fractional distillation or fractional crystallisation. All these process steps can be carried out in batch, continuous or semi-continuous modes.

It is to be understood that the above mentioned embodiments are described solely for purposes of illustration and that combinations of these or similar variations not specifically described are also included within the present invention.

In the process of the present invention, the amount of hydrogen chloride which can be added to aniline before formation of deleterious solids, within the temperature range typically employed in the aniline/formaldehyde condensation stage of conventional DADPM processes (ca. 40 to 75° C.), has been found from the measured results presented in the table below to follow the relationship:—

Wt % HCl=1.43×[water]+0.07$T$−0.55 where [water] is the concentration of water in the aniline, expressed as weight percent and T is the temperature of the aniline/water mixture, expressed in degrees Celcius.

| Temp | $H_2O$ % w/w | HCl % |
|---|---|---|
| 40° C. | 0.1 | 2.4 |
| | 0.3 | 2.6 |
| | 1.9 | 5.2 |
| | 3.2 | 6.8 |
| | 3.1 | 7.2 |
| | 4.3 | 8.3 |
| 60° C. | 0.1 | 3.5 |
| | 0.3 | 3.8 |
| | 1.8 | 6.1 |
| | 3.0 | 7.7 |
| | 3.1 | 8.0 |
| | 4.2 | 9.1 |
| 75° C. | 0.1 | 4.5 |
| | 0.2 | 5.0 |
| | 1.6 | 7.8 |
| | 2.9 | 9.2 |
| | 3.9 | 10.6 |
| | 0.2 | 5.1 |
| | 1.6 | 7.5 |
| | 2.8 | 9.3 |
| | 3.9 | 10.5 |

The beneficial effect in terms of increasing the hydrogen chloride absorption limit before solids formation has also been investigated when adding protic solvents other than water to the aniline. For example, results with methanol indicate that significantly more hydrogen chloride can be retained in solution in aniline mixed with methanol than in its absence, the exact amount also being dependent on the level of added water.

| | methanol (% w/w) | | |
|---|---|---|---|
| % HCl (w/w) | 0 | 2 | 4 |
| 0.27% (w/w) $H_2O$ | 2.6 | 3.5 | 4.5 |
| 1.9% (w/w) $H_2O$ | 5.1 | 5.8 | 6.5 |
| 3.2% (w/w) $H_2O$ | 6.7 | 7.4 | 7.9 |

Mixing water and aniline in controlled amounts to obtain the desired mixture and achieving the desired temperature for the mixture can be carried out by any known method.

In one particular embodiment, the aniline/water mixture is fed to an agitated vessel, where the hydrogen chloride gas is absorbed into the liquid by means of an injection nozzle. Any HCl vapors passing through the liquid rise upwards where they pass into a packed absorption column which is continuously fed from near the top with a small amount of aniline. This aniline absorbs the relatively small proportion of HCl which has passed through the liquid in the vessels and then combines with the bulk aniline/water/HCl mixture. The mixture can then be transferred to subsequent parts of the process. Inert gases which are not absorbed in the aniline/water/HCl mixture can be removed from the top of the absorber column.

It has also been found that if the HCl is taken from a phosgenation plant for use in the present invention, the HCl need not be completely pure. Trace gases which may be considered inert in the DADPM process (carbon monoxide, carbon dioxide and nitrogen) cause no significant problems, whilst traces of residual phosgene can be tolerated because the diphenyl urea which can form from the reaction of phosgene with aniline has been found to be soluble in the reacting DADPM mixture at levels which might reasonably be expected i.e. the urea does not form deleterious solids.

It is to be understood that the description of the present invention is provided for illustrative purposes only. It is to be understood that the present invention may be used in combination with all the known variations of the acid catalysed reaction of aniline and formaldehyde meaning variations in mixing devices, modes of operation (batch, continuous, semi-continuous) and with all variations in recipes and temperature/time reaction profiles and variations in work-up procedures, including neutralisation, which are well understood to affect the final composition of the DADPM, both in terms of major and minor isomers and homologues, and levels of impurities (see, for example, GB 1378423, DD 295628, EP 1403242, EP 1561746, U.S. Pat. No. 6,433,219, U.S. Pat. No. 6,673,970, US 2003/045745 and prior art cited therein).

Further embodiments of processes for manufacturing DADPM using gaseous HCl can also be considered:—

The gaseous HCl may be added fully or in part, in whatever fraction is advantageous, to the aniline/water mixture at the start of the process and further additions of gaseous HCl may be added at subsequent times during the DADPM process. The exotherm arising from the addition of the HCl may optionally be used as part of the overall heating up of the reaction mixture.

The gaseous HCl may also be added to the mixture formed by reaction of aniline and formaldehyde in neutral or basic conditions (so called "neutral condensation" processes where the initial compounds formed include methylene di-aniline ("aminal").

Gaseous HCl may also be used in combination with aqueous HCl in a range of proportions. In addition, the DADPM resulting from any such processes may be used in combination with any of the various known phosgenation processes to produce PMDI.

The various aspects of this invention are illustrated, but not limited by the following examples.

COMPARATIVE EXAMPLE 473.1 g of aniline were put into a 1 litre stirred reactor and 155.9 g of 30.75% aqueous hydrochloric added. The temperature was equilibrated at 60° C. 165.5 g of 44.1% aqueous formalin was added slowly over the course of 20 minutes, the temperature being allowed to rise to 80° C. This temperature was maintained for 15 minutes. The ratio of starting materials (aniline:formaldehyde:HCl) was thus 2.09:1.00:0.54 molar. The water content of the mixture, including the water of reaction, is thus 30.9 wt %. The temperature was then increased at a rate of 1.6° C./min up to 120° C. The reacting mixture was held at this temperature for a further 20 minutes. The reaction mixture was cooled and neutralised with excess sodium hydroxide solution. The organic and aqueous phases were allowed to separate. Subsequent analysis showed the diamine content of the polymeric DADPM to be 56.2 wt % and the triamine content to be 24.4%. The 2,4'-MDA content of the diamine fraction was found to be 8.3%.

EXAMPLE 1

473 g of aniline containing 6.4 wt % water were put into a 1 litre stirred reactor and 44.6 g of hydrogen chloride gas were added from a cylinder. The temperature was equilibrated at 60° C. No solid materials could be observed. 165.4 g of 44.1% aqueous formalin was added slowly over the course of 20 minutes, the temperature being allowed to rise to 80° C. This temperature was maintained for 14 minutes. The ratio of starting materials was thus 2.09:1.00:0.50 molar. The water content of the mixture, including the water of reaction, is thus 23.4 wt %. The temperature was then increased at a rate of 1.6° C./min up to 120° C. The reacting mixture was held at this temperature for a further 20 minutes. The reaction mixture was cooled and neutralised with excess sodium hydroxide solution. The organic and aqueous phases were allowed to separate. Subsequent analysis showed the diamine content of the polymeric DADPM to be 56.4 wt % and the triamine content to be 24.4%. The 2,4'-MDA content of the diamine fraction was found to be 9.3%.

EXAMPLE 2

473 g of aniline containing 2.1 wt % water were put into a 1 litre stirred reactor and 45.3 g of hydrogen chloride gas were added from a cylinder. The temperature was equilibrated at 60° C. Solid materials could be observed.

EXAMPLE 3

473.6 g of aniline containing 2.1 wt % water were put into a 1 litre stirred reactor and 23.5 g of hydrogen chloride gas were added from a cylinder. The temperature was equilibrated at 60° C. No solid materials could be observed. 165 g of 44.1% aqueous formalin was added slowly over the course of 20 minutes, the temperature being allowed to rise to 80° C. This temperature was maintained for 15 minutes, during which a further 23 g of HCl gas were added to the mixture. The ratio of starting materials was thus 2.09:1.00:0.53 molar. The water content of the mixture, including the water of reaction, is thus 21 wt %. The temperature was then increased at a rate of 1.6° C./min up to 120° C. The reacting mixture was held at this temperature for a further 20 minutes. The reaction mixture was cooled and neutralised with excess sodium hydroxide solution. The organic and aqueous phases were allowed to separate. Subsequent analysis showed the diamine content of the polymeric DADPM to be 55.9 wt % and the triamine content to be 24.4%. The 2,4'-MDA content of the diamine fraction was found to be 10.8%.

The differences in diamine contents of the final products are minor and may largely be explained by variations in analysis results. Differences in 2,4'-MDA contents may be partially explained by analysis variations and also relatively minor differences in temperature/time profiles which can not be duplicated exactly between experiments. Impurity levels in all the experiments were at acceptably low levels.

Thus, the above examples show that gaseous HCl can be used in place of aqueous hydrochloric acid within the composition and temperature ranges claimed without significant changes to product quality. The smaller amount of water present in the examples using gaseous HCl would enable greater throughput of reaction mixture in a production plant and result in less aqueous material to be processed in subsequent effluent treatment operations.

The invention claimed is:

1. A process for preparing diamino diphenyl methane and poly(diamino diphenyl methane) comprising:
   (i) preparing an aniline/water mixture having a water content ranging from 0.1 to 7 wt%;
   (ii) introducing hydrogen chloride gas to the mixture of step (i) such that the hydrogen chloride gas is absorbed into the aniline;
   (iii) introducing, optionally with simultaneous mixing, formaldehyde into the mixture of step (ii) in one or more stages, optionally with cooling, to yield an intermediate mixture;
   (iv) heating said intermediate mixture to produce the desired mixture of primary amine isomers and homologues;
   (v) neutralizing the acid typically a sodium hydroxide solution, separation and washing of the organic and brine phases, followed by removal and recycling of excess unreacted aniline.

2. A process for preparing diamino diphenyl methane and poly(diamino diphenyl methane) comprising:
   (i) preparing an aniline/water mixture having a water content typically 0.1 to 7 wt% of water;
   (ii) introducing hydrogen chloride gas, optionally from a phosgenation process, to the mixture of step (i) such that the hydrogen chloride gas is absorbed into the aniline, optionally with cooling to a desired temperature;
   (iii) introducing, optionally with simultaneous mixing, of formaldehyde into the mixture of step (ii) in one or more stages, optionally with cooling, to yield an intermediate mixture;
   (iv) heating said intermediate to predetermined levels ranging from 50° C. to 150° C., optionally in staged increments, to produce the desired mixture of primary amine isomers and homologues;
   (v) neutralizing the acid with a sodium hydroxide solution, separation and washing of the organic and brine phases, followed by removal and recycling of excess unreacted aniline.

3. The process according to claim 1, wherein step (iv) is conducted at a temperature ranging from 50° C. to 150° C.

* * * * *